(12) United States Patent
Olcese (10) Patent No.: US 8,445,436 B2
(45) Date of Patent: May 21, 2013

(54) OXYTOCIN AND MELATONIN COMPOSITIONS AND ASSOCIATED METHODS FOR INDUCING LABOR

(75) Inventor: James Olcese, Tallahassee, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 32 days.

(21) Appl. No.: 12/745,819

(22) PCT Filed: Dec. 3, 2008

(86) PCT No.: PCT/US2008/013317
§ 371 (c)(1),
(2), (4) Date: Jul. 21, 2010

(87) PCT Pub. No.: WO2009/073184
PCT Pub. Date: Jun. 11, 2009

(65) Prior Publication Data
US 2010/0279935 A1    Nov. 4, 2010

Related U.S. Application Data (60) Provisional application No. 60/991,866, filed on Dec. 3, 2007.

(51) Int. Cl.
*A61K 38/11* (2006.01)
*A61K 31/4045* (2006.01)
*C07K 4/00* (2006.01)
*C07K 2/00* (2006.01)

(52) U.S. Cl.
USPC .......................................... 514/11.6; 530/300

(58) Field of Classification Search
None
See application file for complete search history.

(56) References Cited

U.S. PATENT DOCUMENTS
6,743,448 B2 *   6/2004   Kryger .......................... 424/489
2005/0256028 A1 * 11/2005   Yun et al. ........................ 514/2

OTHER PUBLICATIONS
Sharkey et al., J Clin Endocrinol Metab. 2009, 94: 421-427.*
Sarna et al., Anesth Analg 1997; 84: 753-756.*
Mårtensson et al., Eur J Pharmacol. 1996; 316: 273-5.*
Khalifa et al., Bulletin of the Faculty of Pharmacy, Cairo University, 1997; 35(3): 233-37.*
Olcese et al., Reproductive sciences, 00(0) 1-7; May 3, 2012; epublication ahead of print.*
Schlabritz-Loutsevitch et al., J Clin Endocrinol Metab, 2003; 88: 908-913.*
Sharkey and Olcese, J Clin Endocrinol Metab 2007, 92: 4015-1419.*
Shors and Miesegaes, PNAS, 2002; 99: 13955-13960.*
nlm.nih.gov/medlineplus/druginfo/meds/a605020.html (6 pages total).*
rxlist.com/script/main/rxlist.asp?articlekey=65242&pf=3&page=0; 6 pages total.*
latimesblogs.latimes.com/booster_shots/2009/05/testosterone-cream-bad-for-babies-fda-warns; 2 pages total.*
Abstract of Svoren et al., J Pediatr Endocrinol Metab. 2005; 18: 507-10; 1 page.*

* cited by examiner

*Primary Examiner* — Bridget E Bunner
*Assistant Examiner* — Christina Borgeest
(74) *Attorney, Agent, or Firm* — Allen, Dyer, Doppelt, Milbrath & Gilchrist, P.A.

(57) ABSTRACT

The invention discloses a pharmaceutical composition containing oxytocin and melatonin in amounts therapeutically effective for inducing labor in a pregnant human patient. Preferably, the oxytocin content is reduced to mitigate unwanted side effects and the melatonin content synergistically enhances the oxytocin's labor-inducing effectiveness. Also disclosed is a pharmaceutical composition for treatment of a pregnant human patient experiencing pre-term labor characterized by early expression of melatonin receptors in myometrial cells, the composition containing one or more agents which interfere with melatonin binding to said receptors. Additionally, the invention includes a method of treatment effective in inducing labor in a pregnant human patient, the method comprising coadministering melatonin and oxytocin to the patient and a method of treating pre-term labor in a pregnant human patient manifesting early expression of melatonin receptors in her myometrial tissues, the method comprising administering to the patient an agent effective in blocking melatonin binding to the receptors.

8 Claims, 6 Drawing Sheets

FIG. 1A

FIG. 1B
MT2R in NIL myometria

FIG. 1D

FIG. 1C
MT2R in labor

OXYTOCIN AND MELATONIN COMPOSITIONS AND ASSOCIATED METHODS FOR INDUCING LABOR

RELATED APPLICATION

This application claims priority from provisional application Ser. No. 60/991,866 which was filed on 3 Dec. 2007, and which is incorporated herein by reference in its entirety.

STATEMENT OF GOVERNMENT RIGHTS

The invention was made possible through the use of tissues obtained from a tissue bank which is supported by the U.S. Government at least in part. Accordingly, the Government may have certain rights in the invention, as specified by law.

FIELD OF THE INVENTION

The present invention relates to the field of pharmaceutical compositions and, more particularly, to compositions useful in treating pregnant humans to induce labor with reduced side effects.

BACKGROUND OF THE INVENTION

Continuous monitoring of normal uterine contractile activity during late term pregnancy in humans has shown increased frequency between the hours of 8:30 PM and 2:00 AM[1]. Studies on the timing of human labor onset and deliveries show that the initiation of labor peaks between the hours of 24:00 and 05:00, regardless of gestational age[2]. Current models describe parturition as a multi-step process beginning with myometrial activation in late pregnancy followed by stimulation leading to uterine contraction and subsequent delivery of the infant. Myometrial activation encompasses cellular remodeling with appropriate changes in gene expression. The increased expression of these "contraction-associated proteins" marks the transition of the myometrium from a quiescent to activated state. These proteins facilitate the powerful uterine contractions necessary to deliver the infant by increasing the excitability of the myometrial cells, enhancing smooth muscle myosin-actin interactions, and increasing intercellular connectivity, thereby facilitating synchronous myometrial contractions[3].

After its activation the myometrium can be stimulated by multiple factors including oxytocin, prostaglandins and noradrenaline[4,5]. Oxytocin, a nonapeptide hormone secreted by the pituitary gland is one of the most potent uterine contractants. Oxytocin (OT), upon binding to its Gq-protein coupled receptor (OTR), activates the membrane-bound phospholipase C (PLC) and subsequently protein kinase C (PKC). Inositol trisphosphate (IP3), cleaved from membrane phospholipids, binds receptors on the sarcoplasmic reticulum triggering the release of Ca++ from intracellular stores as well as the influx of extracellular Ca++ via membrane calcium channels. Increases in intracellular calcium concentrations result in activation of the Ca++/calmodulindependent enzyme, myosin light chain kinase (MLCK), thereby leading to the phosphorylation of the myosin light chain and also to myometrial contraction[6,7].

Melatonin (MEL), a monoamine hormone secreted by the epithalamic pineal gland, is a major molecular messenger of the nocturnal phase of the light-dark cycle. MEL signals via two G-protein coupled receptors, melatonin receptor 1 (MT1R) and melatonin receptor 2 (MT2R)[8]. We have previously shown that human myometrium is a target for MEL and expresses both melatonin receptors[9,10]. These studies pointed to a potential point of interaction between OT and MEL signaling pathways. An earlier report demonstrated that MEL potentiates norepinephrine-induced contractility in a dose dependent manner in human myometrial strips[11].

Our previous work showed striking similarities between MEL regulation of OTR mRNA expression and the regulation of OTR mRNA expression by OT[10,12] leading us to further explore the similarities between the MEL and OT signaling pathways in the myometrium. Herein, we investigated the effects of MEL on myometrial contractility in vitro by conducting experiments with the well characterized hTERT telomerase-immortalized human myometrial smooth muscle cell line which have been shown to express oxytocin receptors[13]. The results of the present studies show that MEL acts synergistically via the MT2R/PLC/PKC signaling pathway to significantly increase sensitivity of myocytes to OT and increase OT-induced contractility in a dose dependent manner. In addition, we also investigated the potential effects of MEL on expression of the gap junction protein, connexin43 (Cx43). Expression of Cx43 is known to increase late in human pregnancy thereby facilitating myometrial cell coupling and synchronization of uterine contraction[3]. Our data reveal that MEL treatment of cultured myometrial cells increased both mRNA and protein levels of Cx43 via the MT2R signaling cascade. Taken together these studies point to a novel regulatory function of the circadian hormone MEL in "gating" human myometrial activity. More specifically, our data provide a model system to investigate the mechanism through which MEL interacts with the OT pathway to promote uterine contractility and parturition.

SUMMARY OF THE INVENTION

The invention herein disclosed is based on the surprising finding that melatonin acts synergistically with oxytocin to bring about strong, coordinated contractions of human myometrial smooth muscle cells.

With the foregoing in mind, the present invention advantageously provides a pharmaceutical composition containing oxytocin and melatonin in amounts effective for inducing labor in a pregnant human patient. The composition preferably contains an amount of oxytocin which is reduced so as to lower risk of unwanted side effects upon administration to the patient. More specifically, the composition has the oxytocin content reduced to mitigate its unwanted side effects and the melatonin content synergistically enhancing the oxytocin's labor-inducing effectiveness. Such a composition is useful to induce labor in a pregnant human patient.

Conversely, the invention also provides a pharmaceutical composition for treatment of a pregnant human patient experiencing pre-term labor due to early expression of melatonin receptors in myometrial cells, the composition containing one or more inhibitors which interfere with melatonin binding to said receptors. The inhibitor may be selected from inhibitors of MT2R, inhibitors of protein kinase C, inhibitors of phospholipase C, and combinations thereof. This type of composition may be used to treat pre-term labor in a pregnant human patient who manifests the early expression of melatonin receptors in her myometrial tissues.

More broadly viewed, the present invention includes a pharmaceutical composition containing oxytocin and melatonin in amounts effective for causing smooth muscle contractions in a human patient. Preferably, the smooth muscle comprises myometrial tissue and the human patient is a pregnant female.

The invention further includes a method of treatment effective in inducing labor in a pregnant human patient, the method comprising coadministering melatonin and oxytocin to the patient. Another method of the invention includes inducing coordinated contractions in myometrial muscle cells, the method comprising contacting the cells with a composition containing melatonin and oxytocin.

Yet another method of the invention provides for treating pre-term labor in a pregnant human patient manifesting early expression of melatonin receptors in her myometrial tissues, the method comprising administering to the patient an agent effective in blocking melatonin binding to the receptors.

Those skilled in the art will recognize that the compounds of this invention may be administered to mammals, preferably humans, either alone or in combination with pharmaceutically acceptable carriers, excipients or diluents, in a pharmaceutical composition, according to standard pharmaceutical practice. The compounds can be administered by any route but are preferably administered parenterally, including by intravenous, intramuscular, intraperitoneal, subcutaneous, rectal and also by topical routes of administration.

The term "composition" is intended to encompass a product comprising the specified ingredients in amounts effective for causing the desired effect in the patient, as well as any product which results, directly or indirectly, from combination of the specific ingredients. However, the skilled should understand that when a composition according to this invention is administered to a human subject, the daily dosage of active agents will normally be determined by the prescribing physician with the dosage generally varying according to the age, weight, sex and response of the individual patient, as well as the severity of the patient's symptoms.

The terms "treat," "treating" or "treatment" refer to both therapeutic treatment and prophylactic or preventive measures, wherein the object is to either induce or prevent or slow down (lessen) an undesired physiological change. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable.

The term "(therapeutically) effective amount" refers to an amount of the compound of the invention or other agent (e.g., a drug) effective to treat a disease or disorder in a mammal. In the case of induction of labor, an effective amount is sufficient to bring about the desired condition in the patient. In the case of an undesirable pre-term labor an effective amount of an inhibitor or antagonist is sufficient to stop or at least lessen the intensity of the pre-term labor.

The pharmaceutical compositions may be in the form of a sterile injectable aqueous solutions. Among the pharmaceutically acceptable vehicles and solvents that may be employed are water, Ringer's solution and isotonic sodium chloride solution. The phrases pharmaceutically and/or pharmacologically acceptable refer to molecular entities and/or compositions that do not produce an adverse, allergic and/or other untoward reaction when administered to an animal, as appropriate. As used herein, a pharmaceutically acceptable carrier includes any and/or all solvents, dispersion media, coatings, antibacterial and/or antifungal agents, isotonic and/or absorption delaying agents and/or the like. The use of such media and/or agents for pharmaceutical active substances is well known in the art. Except insofar as any conventional media and/or agent is incompatible with the active ingredient, its use in the therapeutic compositions is contemplated. Supplementary active ingredients can also be incorporated into the compositions. For administration, preparations should meet sterility, pyrogenicity, general safety and/or purity standards as required by the Food and Drug Administration's Office of Biologics standards.

BRIEF DESCRIPTION OF THE DRAWINGS

Some of the features, advantages, and benefits of the present invention having been stated, others will become apparent as the description proceeds when taken in conjunction with the accompanying drawings in which:

FIG. 1 shows functional melatonin receptors in the human myometrium; Western blot for the type 2 melatonin receptor (MT2R) in telomerase immortalized human myometrial cells (hTERT), uteroleioma cells stably transfected with either type 1 melatonin receptor (MT1R), the MT2R or neither (neg) (FIG. 1A); MT2R-immunoreactivity in myometrial punches from pregnant non-laboring patients (FIG. 1B); or from patients in active labor (FIG. 1C); Numbers in FIGS. 1B and 1C represent individual donor samples.

FIG. 2 depicts effects of iodomelatonin on oxytocin-induced contractility; A) contractility of hTert myometrial cells treated with oxytocin (OT; dark bars) or co-treated with 1 nM I-MEL (light bars); * $P<0.05$ relative to control values; ** $P<0.05$ relative to all columns marked * B) Effects of treatment with 10 μM of the PKC inhibitor C1, or 10 nM of the MT2R specific antagonist 4P-PDOT, on I-MEL induced contractility; C) effect of 4P-PDOT pretreatment on the contractility of samples co treated with I-MEL and OT; ** $P<0.05$ relative to OT-treated and IMEL/OT/4P-PDOT-treated samples; * $P<0.05$ significantly elevated over controls; D) Effects of treatment with 1 nM of I-MEL (M) and/or oxytocin (OT) on the phosphorylation of the myosin light chain regulatory subunit and the effect of co-treatment with 10 nM 4P-PDOT (PD) or 10 μM C1; Un=untreated control cells; S=size markers;

FIG. 3 shows the effects of iodomelatonin on the expression of the gap junction protein, connexin 43; A) Effects of treatment with 1 nM I-MEL (filled bars) or control vehicle (open bars) on connexin 43 mRNA levels in hTERT cells collected at 0 hr, 4 hr and 8 hr (Mean+SEM; n=9); B) Effects of treatment with I-MEL on connexin 43 protein levels; C) Effect of co-treatment with 4P-PDOT on Cx43 mRNA levels;

DETAILED DESCRIPTION OF A PREFERRED EMBODIMENT

The present invention will now be described more fully hereinafter with reference to the accompanying drawings, in which preferred embodiments of the invention are shown. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. Any publications, patent applications, patents, and other references mentioned herein are incorporated by reference in their entirety. In case of conflict, the present specification, including any definitions, will control. In addition, the materials, methods and examples given are illustrative in nature only and not intended to be limiting. Accordingly, this invention may be embodied in many different forms and should not be construed as limited to the illustrated embodiments set forth herein. Rather, these illustrated embodiments are provided so that this disclosure will be thorough and complete, and will fully convey the scope of the invention to those skilled in the art. Other features and advantages of the invention will be apparent from the following detailed description, and from the claims.

Materials and Methods

Cell Culture

Telomerase immortalized myometrial cells (hTert) were maintained in DMEM/F12 (Mediatech) medium with 10% FBS (Hyclone) with penicillin/streptomycin and gentamycin at 37° C. and 5% $CO_2$. Cells were trypsinized at 90% confluency and plated in T175 cell culture flasks at a 1:5 dilution or 6 well plates at 20,000 cells per well. For pharmacological experiments cells were treated with iodo-melatonin (Tocris; USA), oxytocin (Sigma-Aldrich; USA) or cotreated as described in the Results. Pharmacological inhibitors, 4-phenyl-2-propionamidotetralin (4P-PDOT), a MT2R specific antagonist, the general PKC inhibitor C1, and the phospholipase C inhibitor, U73122 (all from Tocris) were applied as a pretreatment 1 hr prior to application of IMEL or OT. After treatment the cells were trypsinized, pelleted, washed in phosphate-buffered saline, and frozen at −20° C. until further analysis.

Immunoblotting

Frozen myometrial samples from pregnant women before and after the onset of labor and nonpregnant women were obtained from an NIH-funded tissue repository as described previously[14]. Term pregnancy without labor was defined as gestational week 38-40 with no sign of uterine contractions or cervical changes, while term pregnancy with true labor was defined as undergoing at least 3 spontaneous (not induced), regular uterine contractions in a 10 min interval in association with progressive increases in cervical effacement and dilation, or dilation of >4 cm. Uterine contractions in the absence of cervical change were considered "false labor". Myometrial tissues from women with clinical or histological chorioamnionitis, rupture of membranes >12 h, placenta previa, APLA syndrome, abnormal vaginal discharge, or positive myometrial cultures for β-step, gonorrhea, trichomonas or syphilis were also excluded.

For in vitro investigations cultured hTERT cells were collected by trypsinization and gentle scraping. Cells were suspended in PBS and pelleted by centrifugation. Protein extraction was performed according to the method of Shearman and colleagues[15]. Following electrophoretic separation on a 10% SDS-polyacrylamide gel, proteins were semi-dry blotted in buffer onto a Whatman PROTRAN Nitrocellulose membrane (Whatman; Germany). Molecular size markers (Amersham) were included. The membrane was incubated for 60 min at 20° C. in blocking buffer containing 5% milk powder before overnight incubation at 4° C. with anti-OTR, anti-MT2R (Santa Cruz Biotechnology), anti-Cx43 antiserum (Millipore) or anti-actin (Sigma) at a dilution of 1:1000 in blocking buffer. Following washing in buffer (20 mM Tris, pH 7.6+137 M NaCl+0.05% Tween-20), the membrane was incubated at 20° C. for 1 h with a peroxidase-conjugated affinity purified goat anti-rabbit immunoglobulin (Sigma) in a 1:2000 dilution. Chemiluminescent signals were then detected with the Pierce ECL Western Blotting Substrate (Pierce; USA) using CL-X Posure film (Pierce). Western blotting for phospho-myosin light chain kinase (Ser19) (Millipore) was performed with the following exceptions. Membranes were blocked with a 5% BSA/TBS solution for one hour. The primary antibody was diluted in TBS at a 1:500 dilution at 4° C. overnight with shaking. The goat anti-rabbit immunoglobulin was diluted 1:2000 in a 5% milk/TBST solution. Densitometric analysis was performed using AIS Image Analysis software (Ontario, Canada) of images acquired with a digital camera. Criterion for assessment of samples as immunonegative was the absence of a band after 1 hr of exposure. Western blots were repeated a minimum of three times to insure reproducibility.

Myometrial Cell Contractility Assay

Myometrial cell contractility was assayed using a collagen disk retraction assay as described by Devost and Zingg[16] plating 10,000 hTERT cells per well. Samples were treated as described in the Results and each treatment was performed in triplicate. Myometrial cell contractility was quantified by capturing images of the fixed collagen disks with a digital camera and analyzing for total area using AIS Image Analysis Software (Ontario, Canada). The results were normalized to the cell-free control sample areas and expressed as a percentage of untreated control area.

Quantitative PCR

Cellular total RNA was extracted with the RNEasy® kit (QIAGEN; Valencia, Calif., USA) according to the manufacturer's protocol. The RNA concentration was measured with the Nanodrop® photometer and then reverse transcribed to cDNA by means of the iScript® reverse transcription system (Bio-Rad Laboratories; USA). Quantitative real-time PCR was performed on a Bio-Rad iCycler® using iQ SYBR Green Supermix® (Bio-Rad), together with 1 μl of sense and antisense primers (10 μmol/μl) of the transcript of interest and 2 μl of template cDNA. The following thermal cycling parameters were used: initial heat activation of the DNA-polymerase was performed at 95° C. for 5 min. Thereafter 40 cycles at 95° C. (15 sec), 58° C. (30 sec), and 72° C. (30 sec) were run. After thermocycling the iCycler performs an automatic melting curve, which entails cooling to 55° C. for 10 sec and then increasing temperatures in 0.2° C. increments up to 90° C. This controls for primer-dimer formation and other nonspecific effects. Quantification of the data was achieved by the Bio-Rad iCycler software using a standard curve from a primer-specific dilution series for the PCR product. Data were normalized against expression of the housekeeping gene glyceraldehyde-3-phosphate dehydrogenase (GAPDH). The primer sequences used for Cx43, and GAPDH quantification are as follows:

```
Cx43 forward     5'-ATG AGC AGT CTG CCT TTC GT-3';
Cx43 reverse     5'-TCT GCT TCA AGT GCA TGT CC-3';
GAPDH forward    5'-GTC TTC ACC ACC ATG GAG-3';
and
GAPDH reverse    5'-GTC ATG GAT AAC CTT GGC-3'.
```

Lucifer Yellow Dye Migration Assay

Lucifer yellow scrape loading assays were performed in accordance with the procedures of El-Fouly et al[17]. Cells were grown to confluency in 30 mM cell culture dishes, washed with warm phosphate buffered saline (PBS) and treated with 2 mL of pre-warmed 0.05% lucifer yellow in PBS solution. The cells were then scraped by drawing a scalpel across the plate. After two minutes at room temperature the plates were washed three times with prewarmed PBS and returned to normal medium. The plates were then photographed at 10 minutes after scraping using a digital camera through a Zeiss Axiovert 40CFL Microscope at a 100× and 200× magnification. Each treatment condition was repeated three times to ensure reproducibility.

Statistical Analyses

Experiments were repeated a minimum of three times. Replicate values for each data point were averaged and differences statistically analyzed using a one-way ANOVA followed by the Bonferroni post hoc test (Prism; GraphPad, San Diego, Calif., USA) with $P<0.05$ as the criterion level for significance. For testing the observed vs expected percentages of MT2Rimmunopositive myometrial samples, a Chi square test was employed with $P<0.01$ as criterion level.

Results

Figure 1A:
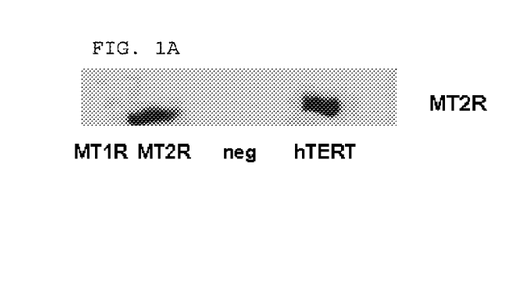
Figure 1B:
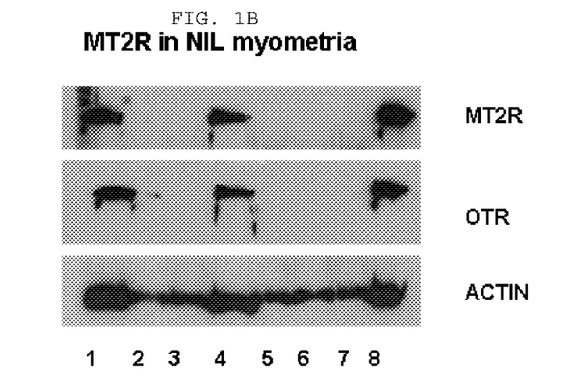
Figure 1C:
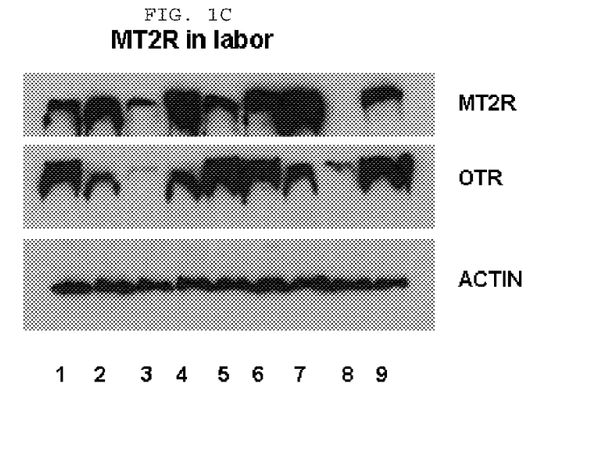
Figure 1D:
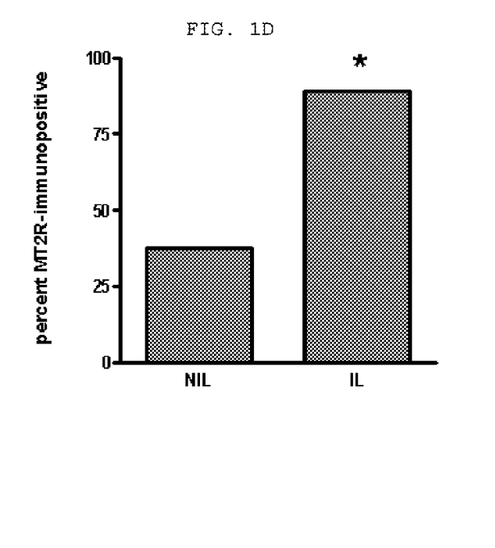
FIG. 1D depicts the results from 1B and 1C in histogram form (* $P<0.05$ by Chi square statistic). E) MT2R mRNA expression in tissues from the same laboring (IL) and non laboring (NIL) patients as in 1B and C (* $P<0.05$ relative to NIL)
Figure 1E:
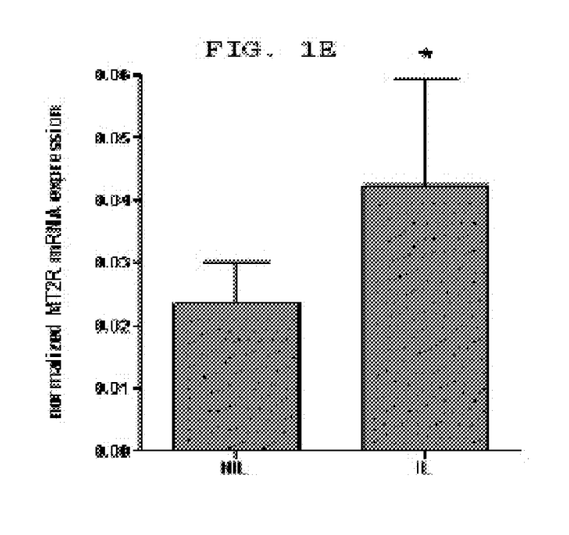

Human myometrium is a target for melatonin. Myometrial tissues express both isoforms of MEL receptors at the transcript and ligand binding levels 9, 10. Using frozen myometrial samples, we conducted immunoblotting experiments and in some cases radioreceptor assays. Western blot analysis was inconclusive using commercial antibodies for MT1R but clearly confirmed the presence of MT2R in both hTERT cells (FIG. 1A) and in term pregnant myometrium. Remarkably, MT2R immunoreactive signals were detected in 89% of myometrial samples from women in labor compared with only 38% of tissues from pregnant women before the onset of labor (FIGS. 1B,C,D). Myometrial tissues from nonpregnant women were completely devoid of MT2R mRNA and immunoreactivity (data not shown). Additional immunoblotting experiments were also conducted to ascertain a potential correlation between OTR and MT2R expression. As shown in FIG. 1B, the MT2R-immunopositive myometria were all likewise OTR-immunopositive, whereas MT2R-negative tissues were typically OTR-negative or in a single case only very weakly OTR-positive. We also found that MT2R mRNA levels were elevated in tissues from laboring patients (FIG. 1E). These results point to a certain degree of regulated co-expression of MT2R and OTR in human myometrial tissue at the time of labor. Additionally, I125-melatonin binding was increased significantly in MT2R-immunopositive tissues (from laboring women) while MEL binding was barely detectable in samples (from nonlaboring women) in which the MT2R was not detected by Western blot (data not shown). This large difference in specific I125melatonin binding implicates the MT2R receptor as the primary site of MEL binding in myometrial smooth muscle (data not shown).

Figure 2A:
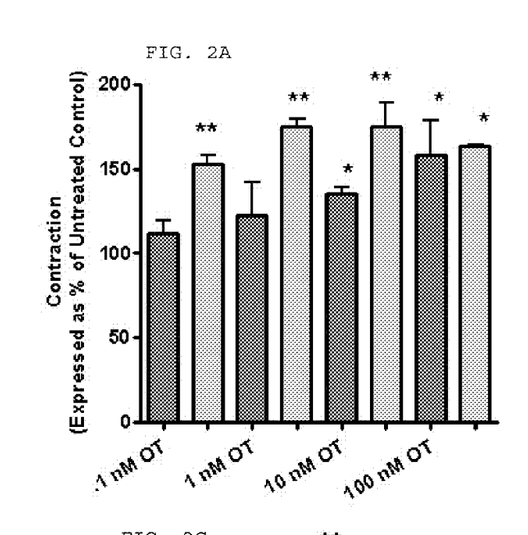
Figure 2B:
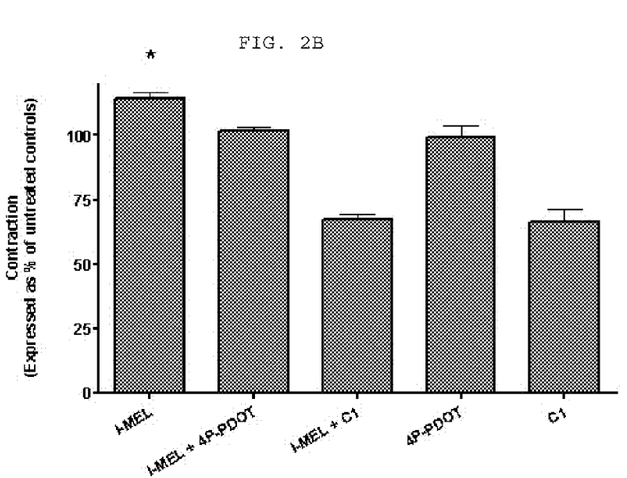
Figure 2C:
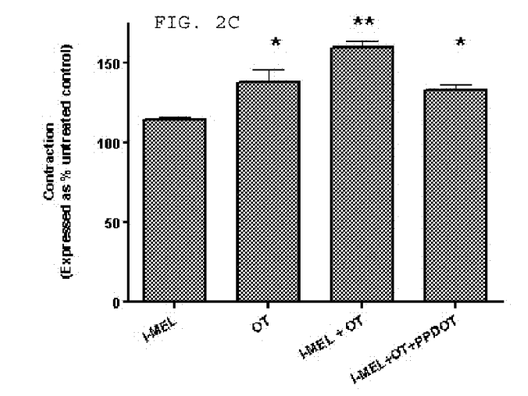
Figure 2D:
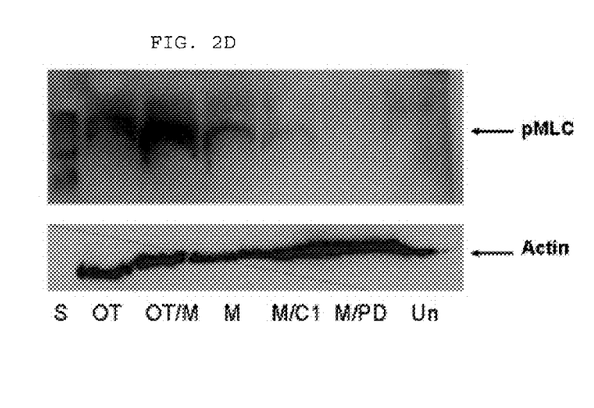

Melatonin increases oxytocin sensitivity and myometrial contractility in vitro via the MT2R/phospholipase C/protein kinase C signaling pathway. Since MEL has been reported to signal via the MT2R to activate Gq mechanisms involving PLC and PKCδ, and these same signaling pathways are utilized by the OTR, we hypothesized that cross talk between the MT2R and OTR might modulate myometrial contractions induced by OT. To investigate this possibility, we performed collagen gel retraction assays in accordance with the published protocols of Devost and Zingg[18]. Co-treatment of cultured hTERT myometrial smooth muscle cells with 1 nM I-MEL and 1 nM OT resulted in a two-fold statistically significant increase in contractility compared to treatment with OT alone. I-MEL acted to increase OT-induced contractility in a dose dependent manner as well as increasing the sensitivity to OT (FIG. 2A). Pharmacological experiments were then conducted with the MT2R specific antagonist 4P-PDOT (10 nM) and the general PKC inhibitor, C1 (10 μM). Treatment with 4P-PDOT reduced the synergistic effect of I-MEL to levels corresponding to treatment with OT alone (FIG. 2C). Treatment with C1 reduced myometrial cell contractility when cells were treated alone or in combination with OT, I-MEL, or both (FIG. 2B). Treatment with the PLC inhibitor, U73122, completely abolished contractility in response to all treatments (data not shown). Western blot analysis for phosphorylated myosin light chain at Ser19 indicated that although I-MEL treatment alone resulted in modest increases in myosin light chain phosphorylation, OT-induced increases in myosin light chain phosphorylation were increased dramatically by I-MEL (FIG. 2D). I-MEL-induced increases in myosin light chain phosphorylation were abolished by 4P-PDOT or C1 pretreatment (FIG. 2D) suggesting that MT2R and PKC are essential for I-MEL-induced increases in myosin light chain phosphorylation.

Figure 3A:
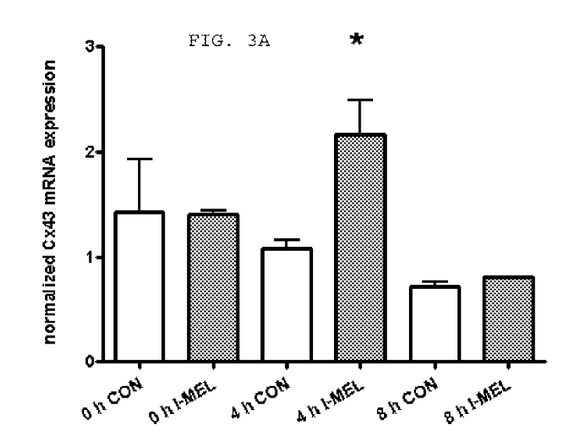
Figure 3B:
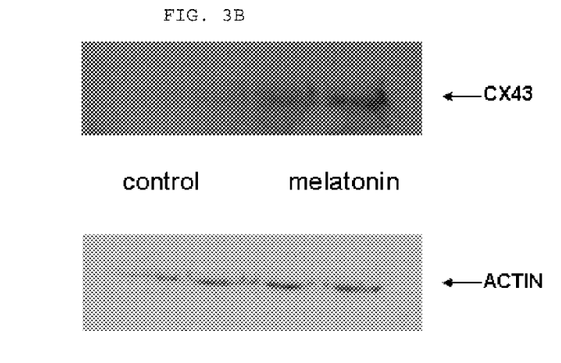
Figure 3C:
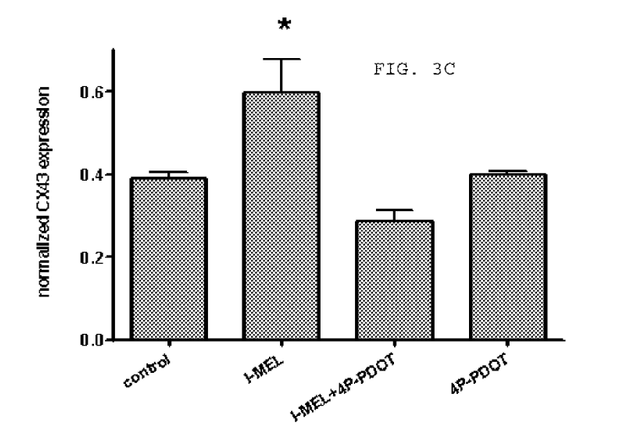

Melatonin increases expression of the gap junction protein Cx43 in vitro through a PKC-dependent pathway. Cx43 expression has been shown to be up-regulated in human myometrium at term and by PKC activation in cultured cells19. Initially we investigated the acute effects of IMEL on Cx43 mRNA levels in cultured hTERT myocytes by quantitative PCR. Treatment with I-MEL (1 nM) resulted in significant, but transient increases in Cx43 mRNA after 4 hrs (FIG. 3A). Western blot analysis confirmed upregulation of Cx43 protein levels in I-MEL-treated cells (FIG. 3B). Co-treatment with 4P-PDOT abolished the effect of I-MEL on Cx43 expression as did treatment with U73122 or C1 (FIG. 3C). These results indicate that induction of myometrial cell Cx43 by I-MEL involves MT2R receptor signaling via PLC and PKC.

To ascertain the effects of I-MEL in a physiological context, we investigated the effects of I-MEL on Cx43 mRNA expression in an 8 hr time course experiment. Cells were treated with I-MEL (1 nM) for 8 hrs to mimic a natural nocturnal phase of the light-dark cycle. Cx43 mRNA levels were assayed at times 0, 4, and 8 hrs. Cx43 mRNA expression was elevated at 4 hrs post MEL treatment but had returned to untreated levels 8 hrs after treatment. These data indicate that Cx43 mRNA expression may be nocturnally stimulated by physiological exposures to MEL (FIG. 3A). The return of Cx43 mRNA expression to control levels after 8 hrs indicates the likely presence of additional methods of regulation of Cx43 mRNA expression.

Figure 4:
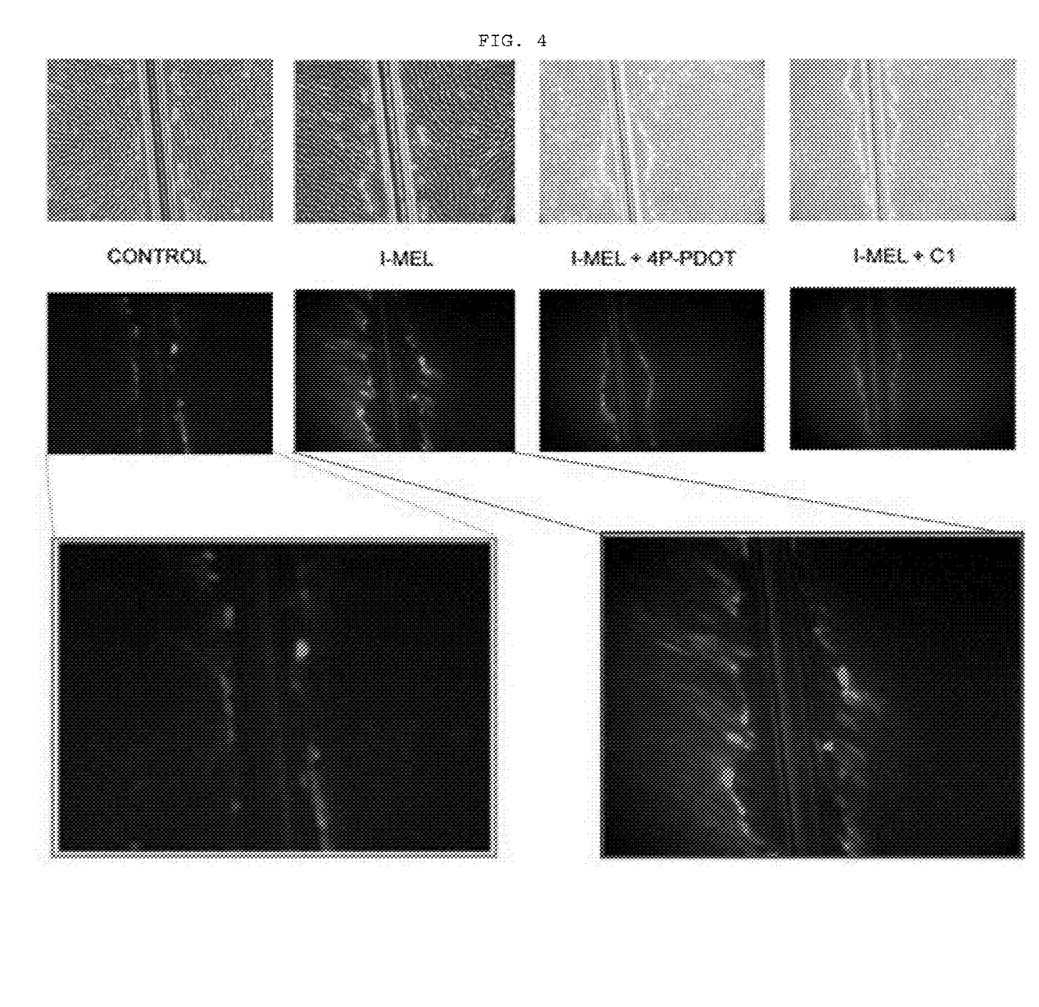
FIG. 4. illustrates effects of melatonin on gap junction communication in hTERT cells; the top row shows the cells under bright field, while the remaining figures were photographed under fluorescent light to demonstrate lucifer yellow dye spread within 10 minutes after scrape loading; treatments included 1 nM I-MEL, or I-MEL after pre-treatment of the cells with 10 nM 4P-PDOT or 10 μM C1; the bottom two images at higher magnification reveal lucifer yellow dye spread in greater detail.

Melatonin increases intercellular connectivity in vitro. I-MEL-induced increases in Cx43 mRNA and protein led us to predict that intercellular communication would be increased due to the formation of additional gap junctions. To test this hypothesis we performed lucifer yellow dye migration assays on I-MEL-treated hTERT cells. Results of these experiments show that the cells from MEL-pretreated plates have increased levels of cell coupling, allowing for a greater spread of the lucifer yellow dye from the site of uptake, an effect which can be blocked by pretreatment with 4P-PDOT or C1 (FIG. 4). Treatment with 4P-PDOT or C1 alone resulted in dye migration comparable to control levels (data not shown).

Discussion

The molecular mechanisms leading to forceful uterine contractions of labor involve many interacting factors and regulatory pathways. Our data present a novel mechanism of interaction of the nocturnal brain hormone MEL with the OT-signaling pathway in human myometrial cells.

These interactions likely occur at multiple points in the signaling cascade. Herein, we demonstrate that co-treatment with physiological concentrations of MEL increases both basal- and OT-induced contractility of myometrial cells and that this stimulatory effect can be blocked by the application of the MT2R specific antagonist 4P-PDOT, the general PKC inhibitor C1, and the phospholipase C inhibitor U73122. From these data it can be concluded that MEL acts synergistically via MT2R to activate PLC, which likely triggers an increase in intracellular calcium. This increase in intracellular Ca++, while presumably sufficient to only modestly augment basal contractility alone (FIG. 2), appears to greatly facilitate OT-induced contractility by sensitizing myometrial cells to OT. Kitazawa previously described a calcium sensitization phenomenon in which PKC resulted in increased force generation in permeabilized uterine strips clamped at a constant Ca++ environment[20]. Since MEL has also been shown to activate PKC in multiple tissues[21], and we have previously reported that MEL regulates OTR expression in myometrial cells through PKC[10], we suggest that MEL not only increases sensitivity to OT through Ca++-sensitization, but also through modulated OTR expression. This agrees with our model that MEL acts synergistically to promote contractility in uterine smooth muscle cells.

OT-induced contractility is initiated by increased phosphorylation of myosin light chain (MLC) at Ser19, which facilitates conformational changes in myosin and interactions with actin. Investigation of I-MEL treatment on MLC phosphorylation (FIG. 2D) showed changes in MLC which agree with our observations from the contractility studies. These data support the conclusion that the responsible receptor is a Gq coupled MT2R rather than a Gi coupled MT2R or MT1R8 which could theoretically augment contractility by suppressing cAMP levels. Although high levels of cAMP have been shown to relax myometrium[3], the myometrium is somewhat refractory to cAMP-induced relaxation relative to other smooth muscles. Our previous work has shown that in this system, melatonin signaling is pertussis toxin-insensitive and PKC-dependent[10] and that MEL treatment inhibits forskolin-induced cAMP accumulation only in myometrial samples from non-pregnant women[9]. Taken together, these findings further strengthen the notion that the synergistic effect of MEL on OT-induced contractility is via MT2R.

MTR and OTR expression levels were similarly different in myometrial samples from non-laboring and laboring women. MT2R immunoreactive signals were detected in 89% of myometrial samples from women in labor but in only 38% of samples from pregnant women not in labor (P<0.05). All samples that were immunopositive for MT2R were also OTR positive. This suggests that low MT2R levels during preterm pregnancy may preclude the synergistic input of MEL on contractility and thus serve to maintain myometrial quiescence. Activation of gene expression at labor also is consistent with the MT2R, like the OTR, being necessary to provide maximum uterine contractility during parturition, and that the nocturnal surges in MEL temporally gate these contractions to occur preferentially at night. To date the regulatory mechanisms underlying gene expression for both the OTR and MTR are poorly understood, indeed our results appear to be the first report of positive regulation of MT2R expression in humans. The similar regulation of both OTR and MT2R and the fact that both serum OT22 and MEL levels[23,24] increase over the course of pregnancy support our hypothesis that MEL acts synergistically to promote OT-induced contractility in pregnant women at term.

Activation of myometrium late in gestation is associated with marked increases in gap junction proteins. The increase in gap junctions is thought to facilitate greater communication between myometrial cells to allow for synchronized contractions. Cx43 protein is the primary component of myometrial gap junctions in term myometrium[3, 19]. We show here that unlike OT which to date has been shown to have little effect on Cx43 protein levels and gap junction formation in humans[25]-I-MEL treatment results in significant increases in Cx43 mRNA and protein levels, and that it leads to increased intercellular coupling between uterine myocytes. These data indicate that MEL promotes contractility not only through direct action on the contractile machinery, but it also acts to facilitate synchronized contractions via increased gap junction-mediated intercellular communication. Both actions would enhance nocturnal uterine contractility at term.

Figure 5:
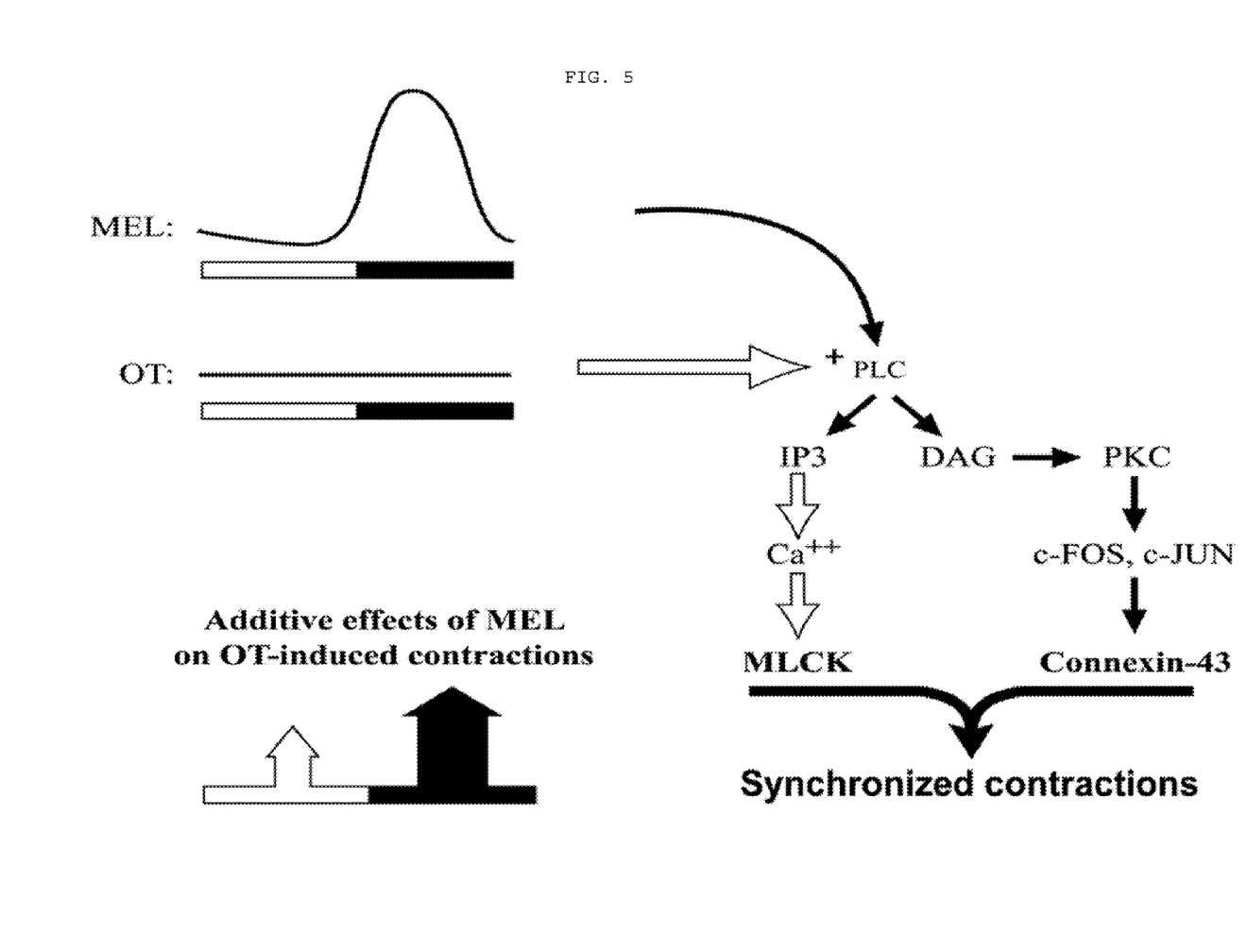
FIG. 5 is a diagram of our proposed model for the synergy between melatonin (MEL) and oxytocin (OT) on nocturnal myometrial contractility in the laboring pregnant uterus; melatonin acts synergistically with OT to increase phospholipase C (PLC) activity and associated signaling mechanisms, thereby enhancing myometrial contractility and gap junction-associated intercellular communication.

In conclusion, while not wishing to be bound to this hypothesis, the model shown in FIG. 5 is proposed to explain the action of MEL in promoting nocturnal contractility during labor. Release of MEL from the pineal gland into the circulation at night leads to binding of MEL to myometrial MT2Rs. Bound MEL activates PLC which generates IP3 and increases intracellular calcium thus activating MLCK. The phosphorylation of MLC results in increased contractility and enhanced sensitivity to OTR-mediated signals. Additionally, the DAG released by MEL binding to the MT2R activates PKC, which has been shown to act via c-fos and c-jun to increase Cx43 expression[26]. It is important to note that modest increases in hTERT contractility in vitro by I-MEL alone were always detected. However, the greatest increases in contractility were achieved when both I-MEL and OT were provided concomitantly. We propose that this neuroendocrine synergy plays a key role in the increase in births observed in the late evening and early morning in humans.

The results of this study point to MEL playing a pro-contractile role in human myometrial physiology during pregnancy. Combined with our previous observations regarding the action of I-MEL on OTR mRNA expression, it appears that MEL and OT signaling is very similar in the human myometrium. These data provide new insights into the mechanisms underlying the timing of birth and regulation of the contractile machinery in the myometrium. Additionally, they reveal a novel physiological interaction whose further characterization may serve in the development of new pharmacological strategies for the management of preterm and/or delayed parturition.

For example, it is well known that administration of oxytocin at levels sufficient to induce labor may also produce unwanted side effects in the patient. With the present results in mind, it becomes apparent that melatonin could be coadministered with oxytocin to synergistically enhance the effect on the uterine musculature and that, accordingly, the amount of oxytocin in the two-agent composition could be lowered sufficiently to minimize its untoward side effects. Therefore, a composition containing oxytocin and melatonin would be expected to be at least as or more effective than oxytocin alone to induce labor.

Additionally, it is proposed that some patients experiencing pre-term labor may be expressing MEL receptors early in myometrial tissues. This early appearance of the MEL receptors would render the patient susceptible to the labor-inducing action promoted by MEL. Therefore, these patients would benefit from the administration of an antagonist or inhibitor that would interfere with the binding of MEL to these early expressed receptors, thereby ameliorating the pre-term labor.

Based on the present discovery, that melatonin acts to synergistically enhance the tissue contractile response of myometrial cells to oxytocin, the inventor further suggests that additional melatonin synergistic signaling mechanisms remain to be yet discovered and applied to the development of drug compositions useful in the treatment of various conditions. Potential examples of these synergistic relationships may include melatonin and vasopressin, melatonin and adrenergics, melatonin and nitric oxide/cGMP signaling.

Accordingly, in the drawings and specification there have been disclosed typical preferred embodiments of the invention and although specific terms may have been employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

REFERENCES

1. Zahn, V. & Hattensperger, W. (1993) [Circadian rhythm of pregnancy contractions]. *Z Geburtshilfe Perinatol*, 197, 1-10.
2. Seron-Ferre, M., Ducsay, C. A. & Valenzuela, G. J. (1993) Circadian rhythms during pregnancy. *Endocr Rev*, 14, 594-609.
3. Smith, R. (2007) Parturition. *N Engl J Med*, 356, 271-283.
4. Blanks, A. M., Shmygol, A. & Thornton, S. (2007) Preterm labour. Myometrial function in prematurity. *Best Pract Res Clin Obstet Gynaecol*, 21, 807-819.
5. Berg, G., Andersson, R. G. & Ryden, G. (1986) Alpha-adrenergic receptors in human myometrium during pregnancy. *Am J Obstet Gynecol*, 154, 601-606.
6. Arthur, P., Taggart, M. J. & Mitchell, B. F. (2007) Oxytocin and parturition: a role for increased myometrial calcium and calcium sensitization? *Front Biosci*, 12, 619-633.
7. Word, R. A., Tang, D. C. & Kamm, K. E. (1994) Activation properties of myosin light chain kinase during contraction/relaxation cycles of tonic and phasic smooth muscles. *J Biol Chem*, 269, 21596-21602.
8. Masana, M. I. & Dubocovich, M. L. (2001) Melatonin receptor signaling: finding the path through the dark. *Sci STKE*, 2001, PE39.
9. Schlabritz-Loutsevitch, N., Hellner, N., Middendorf, R., Muller, D. & Olcese, J. (2003) The human myometrium as a target for melatonin. *J Clin Endocrinol Metab*, 88, 908-913.
10. Sharkey, J. & Olcese, J. (2007) Transcriptional inhibition of oxytocin receptor expression in human myometrial cells by melatonin involves protein kinase C signaling. *J Clin Endocrinol Metab*, 92, 4015-4019.
11. Martensson, L. G., Andersson, R. G. & Berg, G. (1996) Melatonin together with noradrenaline augments contractions of human myometrium. *Eur J Pharmacol*, 316, 273-275.
12. Phaneuf, S., Asboth, G., Carrasco, M. P., Linares, B. R., Kimura, T., Harris, A. & Bernal, A. L. (1998) Desensitization of oxytocin receptors in human myometrium. *Hum Reprod Update*, 4, 625-633.
13. Condon, J., Yin, S., Mayhew, B., Word, R. A., Wright, W. E., Shay, J. W. & Rainey, W. E. (2002) Telomerase immortalization of human myometrial cells. *Biol Reprod*, 67, 506-514.
14. Word, R. A., Tang, D. C. & Kamm, K. E. (1994) Activation properties of myosin light chain kinase during contraction/relaxation cycles of tonic and phasic smooth muscles. *J Biol. Chem.*, 269, 21596-21602.
15. Shearman, L. P., Sriram, S., Weaver, D. R., Maywood, E. S., Chaves, I., Zheng, B., Kume, K., Lee, C. C., van der Horst, G. T., Hastings, M. H. & Reppert, S. M. (2000) Interacting molecular loops in the mammalian circadian clock. *Science*, 288, 1013-1019.
16. Devost, D. & Zingg, H. H. (2007) Novel in vitro system for functional assessment of oxytocin action. *Am J Physiol Endocrinol Metab*, 292, E1-6.
17. El-Fouly, M. H., Trosko, J. E. & Chang, C.-C. (1987) Scrape loading and dye transfer: A rapid and simple technique to study gap junctional intercellular communication. *Experimental Cell Research*, 168, 422-430.
18. Devost, D. & Zingg, H. H. (2007) Novel in vitro system for functional assessment of oxytocin action. *Am J Physiol Endocrinol Metab*, 292, E1-6.
19. Geimonen, E., Boylston, E., Royek, A. & Andersen, J. (1998) Elevated connexin43 expression in term human myometrium correlates with elevated c-Jun expression and is independent of myometrial estrogen receptors. *J Clin Endocrinol Metab*, 83, 1177-1185.
20. Kitazawa, T., Kobayashi, S., Horiuti, K., Somlyo, A. V. & Somlyo, A. P. (1989) Receptor-coupled, permeabilized smooth muscle. Role of the phosphatidylinositol cascade, G-proteins, and modulation of the contractile response to $Ca^{2+}$. *J Biol Chem*, 264, 5339-5342.
21. Sampson, S. R., Lupowitz, Z., Braiman, L. & Zisapel, N. (2006) Role of protein kinase Calpha in melatonin signal transduction. *Mol Cell Endocrinol*, 252, 82-87.
22. Gimpl, G. & Fahrenholz, F. (2001) The oxytocin receptor system: structure, function, and regulation. *Physiol Rev*, 81, 629-683.
23. Kivela, A. (1991) Serum melatonin during pregnancy. *Acta Endocrinol* (Copenh), 124, 233-237.
24. Kivela, A., Kauppila, A., Leppaluoto, J. & Vakkuri, O. (1989) Serum and amniotic fluid melatonin during human labor. *J Clin Endocrinol Metab*, 69, 10651068.
25. Ciray, H. N., Backstrom, T. & Ulmsten, U. (1998) Ineffectiveness of oxytocin on intercellular communication between term pregnant human myometrial cells before labor. *American Journal of Obstetrics & Gynecology*, 178, 855-861.
26. Mitchell, J. A. & Lye, S. J. (2001) Regulation of connexin43 expression by c-fos and c-jun in myometrial cells. *Cell Commun Adhes*, 8, 299-302.

That which is claimed:

1. A pharmaceutical composition containing oxytocin and melatonin in amounts therapeutically effective for inducing labor in a pregnant human patient.

2. The composition of claim 1, wherein the amount of oxytocin is reduced so as to lower risk of unwanted side effects upon administration to the patient.

3. The composition of claim 1, wherein the oxytocin content is reduced to mitigate its unwanted side effects and wherein the melatonin content synergistically enhances the oxytocin's labor-inducing effectiveness.

4. A pharmaceutical composition containing oxytocin and melatonin in amounts therapeutically effective for causing smooth muscle contractions in a pregnant human patient.

5. The composition of claim 4, wherein the smooth muscle comprises myometrial tissue.

6. A method of treatment effective in inducing labor in a pregnant human patient, the method comprising administering the pharmaceutical composition of claim 1 to the patient.

7. A method of inducing coordinated contractions in myometrial muscle cells in a pregnant human patient, the method comprising contacting the cells with the pharmaceutical composition of claim 4.

8. A pharmaceutical composition comprising oxytocin and melatonin in amounts synergistically effective for inducing labor in a pregnant human patient.

* * * * *